(12) United States Patent
Imamura et al.

(10) Patent No.: US 8,888,224 B2
(45) Date of Patent: Nov. 18, 2014

(54) IMAGE READING APPARATUS, IMAGE INSPECTION APPARATUS, PRINTING APPARATUS, AND CAMERA POSITION ADJUSTMENT METHOD

(75) Inventors: Atsushi Imamura, Kyoto (JP); Shiro Koike, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 148 days.

(21) Appl. No.: 13/637,236

(22) PCT Filed: Mar. 17, 2011

(86) PCT No.: PCT/JP2011/056453
§ 371 (c)(1),
(2), (4) Date: Sep. 25, 2012

(87) PCT Pub. No.: WO2011/122360
PCT Pub. Date: Oct. 6, 2011

(65) Prior Publication Data
US 2013/0016154 A1  Jan. 17, 2013

(30) Foreign Application Priority Data
Mar. 30, 2010  (JP) .............................. P2010-076759

(51) Int. Cl.
| | |
|---|---|
| *B41J 29/393* | (2006.01) |
| *G06F 15/00* | (2006.01) |
| *H04N 1/193* | (2006.01) |
| *H04N 1/00* | (2006.01) |
| *G01N 21/89* | (2006.01) |
| *G06K 9/20* | (2006.01) |

(52) U.S. Cl.
CPC ........... *H04N 1/00326* (2013.01); *H04N 1/193* (2013.01); *H04N 1/00334* (2013.01); *G01N 21/8903* (2013.01); *H04N 1/1932* (2013.01); *G06K 9/20* (2013.01)
USPC ............................................. 347/19; 358/1.9

(58) Field of Classification Search
CPC .. B41J 2/16585; B41J 2202/21; B41J 29/393; H04N 1/00326
USPC ................................................ 347/19; 358/1.9
See application file for complete search history.

(56) References Cited

U.S. PATENT DOCUMENTS 8,310,733 B2 * 11/2012 Sekiguchi et al. ............. 358/1.9
8,610,978 B2 * 12/2013 Ishido ............................ 358/1.9
(Continued)

FOREIGN PATENT DOCUMENTS

| JP | 2-306370 | 12/1990 |
|---|---|---|
| JP | 4-166749 | 6/1992 |

(Continued)

OTHER PUBLICATIONS

International Preliminary Report on Patentability of PCT/JP2011/056453 with English translation, mailed Nov. 1, 2012.

(Continued)

*Primary Examiner* — Jannelle M LeBron
(74) *Attorney, Agent, or Firm* — Ostrolenk Faber LLP

(57) ABSTRACT

An image reading apparatus includes two color line cameras and one monochrome line camera and captures a linear imaging area on printing paper. The imaging area is irradiated with illumination light by a line illumination part. When inspecting a printed image, a color image captured with the color line cameras and an original image are compared. An information element image such as a bar code is clipped from a monochrome image captured with the monochrome line camera, and target information indicated by an information element(s) is acquired. In the image reading apparatus, since the color image and the monochrome image are acquired from the same imaging area, it is possible to realize downsizing of the line illumination part and downsizing of the image reading apparatus.

16 Claims, 7 Drawing Sheets

(56) References Cited

U.S. PATENT DOCUMENTS

| | | | |
|---|---|---|---|
| 2001/0019619 A1 | 9/2001 | Watanabe et al. | 382/101 |
| 2007/0235542 A1 | 10/2007 | Tsutsumi | 235/454 |

FOREIGN PATENT DOCUMENTS

| | | |
|---|---|---|
| JP | 2001-243458 | 9/2001 |
| JP | 2001-277676 | 10/2001 |
| JP | 2005-209037 | 8/2005 |
| JP | 2006-079571 | 3/2006 |
| JP | 2007-282214 | 10/2007 |

OTHER PUBLICATIONS

International Search Report mailed May 10, 2011 in corresponding PCT International Application No. PCT/JP2011/056453.

Written Opinion mailed May 10, 2011 in corresponding PCT International Application No. PCT/JP2011/056453.

* cited by examiner

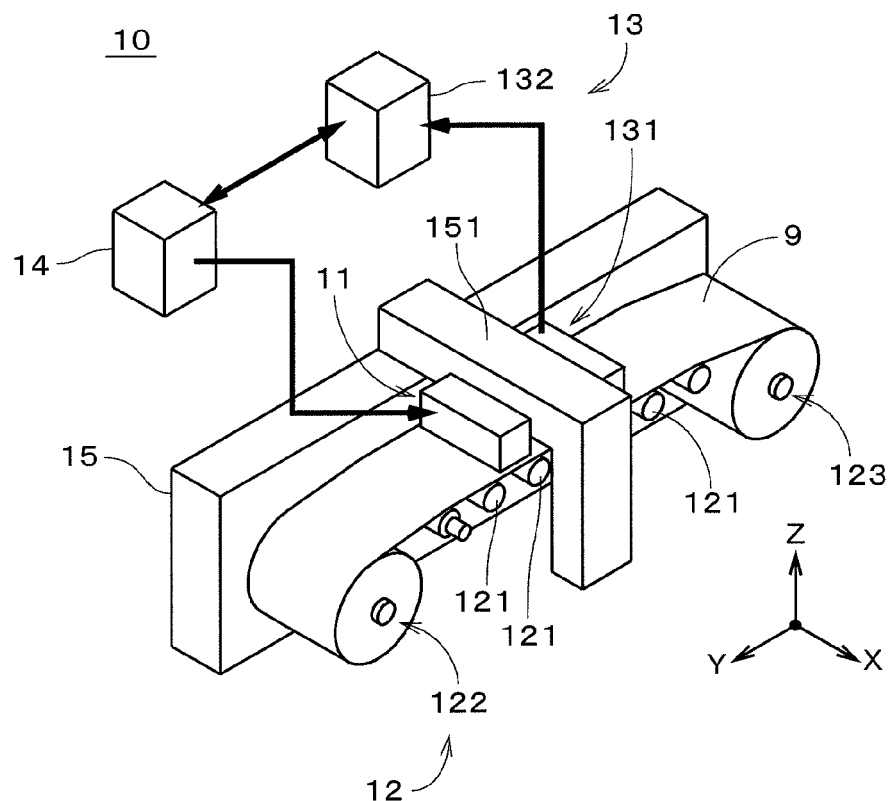

IMAGE READING APPARATUS, IMAGE INSPECTION APPARATUS, PRINTING APPARATUS, AND CAMERA POSITION ADJUSTMENT METHOD

CROSS-REFERENCE TO RELATED APPLICATIONS

The present application is a 35 U.S.C. §§371 national phase conversion of PCT/JP2011/056453, filed Mar. 17, 2011, which claims priority of Japanese Patent Application No. 2010-076759, filed Mar. 30, 2010, the contents of which are incorporated herein by reference. The PCT International Application was published in the Japanese language.

TECHNICAL FIELD

The present invention relates to an image reading apparatus for reading an image printed on a printing medium.

BACKGROUND ART

In recent years, high-speed printing of direct mails or the like has been performed using inkjet printing apparatuses. With such printing apparatuses, an individual piece of information (so-called variable information) is printed on a portion of printing paper that corresponds to each page, the printing paper being roll paper. In images printed by the inkjet printing apparatuses (hereinafter referred to as "printed images"), ink dripping due to the heads of the printing apparatuses rubbing against printing media, or dot missing due to nozzle clogging may occur. Accordingly, an inspection apparatus for detecting such a defect is installed in the printing apparatuses. For example, in the case of color printing, the inspection apparatuses capture a printed image with a color line camera and detect a defect based on the captured image.

Furthermore, there are cases in which printing apparatuses print information elements such as characters, numbers, bar codes, or two-dimensional codes that represent character information or numerical information. Thus, it has been proposed to inspect these information elements in a printed image. For example, Japanese Patent Application Laid-Open No. 2006-79571 discloses a technique in which text printed on paper is recognized, decoded, and converted into a character code and then compared and checked against a character code to be printed, so that it is determined whether the printed text is acceptable or not. In an image recognition apparatus disclosed in Japanese Patent Application Laid-Open No. 2001-277676, three verification fields on paper on which a telephone number or the like has been printed are captured with three OCR (optical character reader) cameras so that it is determined whether print quality is acceptable or not.

In recent years, there is demand for simultaneous inspections of a printed color image and printed information. In such a case, if an inexpensive color line camera that has a low line rate is used in an inspection apparatus, the imaging range taken in a single imaging operation on a fast-moving printing medium is expanded, and the captured image will appear in a state of being compressed in the direction of movement of the printing medium. As a result, for example, if the printed image includes a one-dimensional bar code in which bars are aligned in the direction of movement of the printing medium, the captured one-dimensional bar code will appear in a state in which adjacent bars overlap one another into a single bar, and thus decoding processing cannot be performed. If, as a countermeasure to this, a high-speed monochrome line camera unit that includes an illumination system is provided for decoding processing, separately from the unit used in color image inspection, the size of the inspection apparatus increases and inlining becomes difficult.

SUMMARY OF INVENTION

The present invention is intended for an image reading apparatus for reading an image printed on a relatively moving printing medium, and it is an object of the present invention to downsize the image reading apparatus.

The image reading apparatus according to the present invention is an image reading apparatus for reading an image printed on a relatively moving printing medium. The image reading apparatus includes a line illumination part that applies light onto a linear imaging area on a printing medium, the imaging area extending in a direction crossing with a direction of relative movement of the printing medium, one monochrome line camera that captures the imaging area, or a plurality of monochrome line cameras that capture the imaging area with imaging ranges of the cameras being aligned in a longitudinal direction of the imaging ranges, and a plurality of color line cameras that capture the imaging area with imaging ranges of the cameras being aligned in a longitudinal direction thereof. The number of the plurality of color line cameras is greater than the number of the one or plurality of monochrome line cameras, and each color line camera has a smaller number of pixels than each monochrome line camera.

Preferably, an optical axis of the one or plurality of monochrome line cameras and optical axes of the plurality of color line cameras are parallel to each other, and at least one optical element is common to an optical system between the one or plurality of monochrome line cameras and the printing medium and an optical system between the plurality of color line cameras and the printing medium. As a result, it is possible to simplify the structure of the optical systems.

The present invention is also intended for an image inspection apparatus for inspecting an image printed on a relatively moving printing medium. The image inspection apparatus includes the image reading apparatus, an information image extraction part that extracts an information element image from an image acquired with the one or plurality of monochrome line cameras, the information element image being a portion corresponding to an information element that is at least one of letters, numbers, symbols, and bar code patterns, an information acquisition part that acquires target information from the information element image, the target information being character information or numerical information indicated by the information element, a storage part that stores the target information, and an image comparison part that compares an image acquired with the plurality of color line cameras and an image indicated by data used in printing.

Preferably, the one or plurality of monochrome line cameras is one monochrome line camera. This eliminates the need to combine images captured with a plurality of monochrome line cameras and makes it possible to easily acquire an information element image.

The present invention is also intended for a printing apparatus that includes an image inspection apparatus. The printing apparatus further includes a conveying mechanism that conveys a printing medium, and a printing mechanism that performs printing on the printing medium.

The present invention is also intended for a camera position adjustment method for adjusting positions of a plurality of cameras in an image reading apparatus that reads an image printed on a relatively moving printing medium. The image reading apparatus includes a line illumination part that applies light onto a linear imaging area on a printing medium, the imaging area extending in a direction crossing with a direction of relative movement of the printing medium, one monochrome line camera that captures the imaging area, and a plurality of color line cameras that capture the imaging area with imaging ranges of the cameras being aligned in a longitudinal direction thereof.

The camera position adjustment method includes a step of adjusting a position of the monochrome line camera, a step of adjusting brightness of illumination by the line illumination part with reference to an output from the monochrome line camera, and a step of capturing a reference pattern with the monochrome line camera and the plurality of color line cameras and adjusting the imaging ranges of the plurality of color line cameras with reference to the output from the monochrome line camera and outputs from the plurality of color line cameras. As a result, it is possible to easily adjust joint portions between the imaging ranges of the color line cameras.

These and other objects, features, aspects and advantages of the present invention will become more apparent from the following detailed description of the present invention when taken in conjunction with the accompanying drawings.

BRIEF DESCRIPTION OF DRAWINGS

FIG. 1 shows a printing apparatus according to a first embodiment;

FIG. 2 shows an ejection part in a printing mechanism;

DESCRIPTION OF EMBODIMENTS

Figure 3:
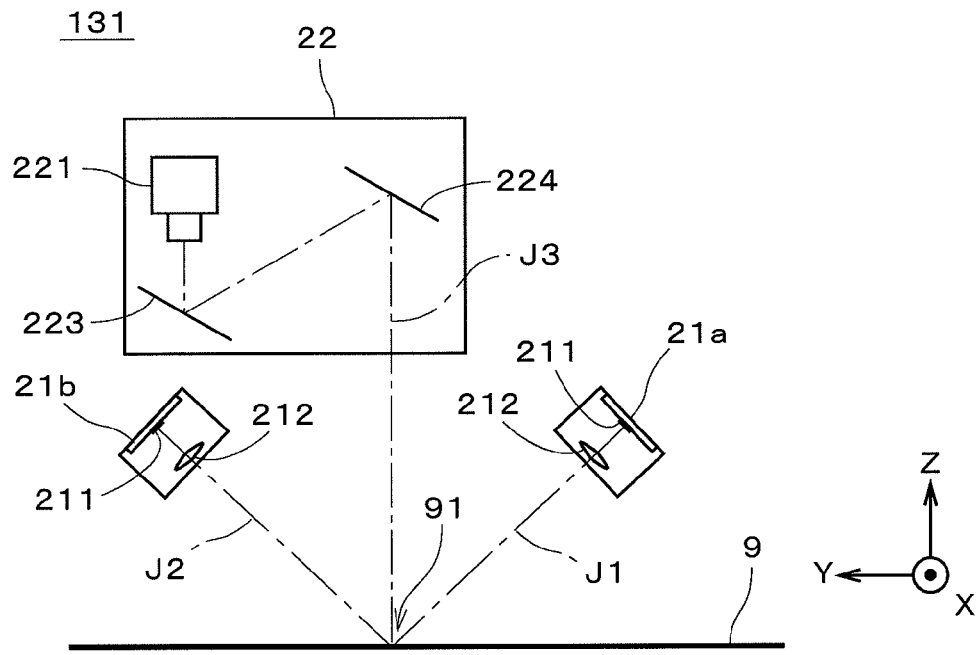
FIG. 3 shows an image reading apparatus.

FIG. 1 is a perspective view showing an external view of a printing apparatus 10 according to a first embodiment of the present invention. In the following description, forming an image on a medium using an inkjet system is referred to as "printing" as appropriate. The printing apparatus 10 includes a printing mechanism 11 for performing printing on printing paper 9 that is web paper, a conveying mechanism 12 for conveying the printing paper 9, an image inspection apparatus 13 that inspects an image, and a control part 14 that controls these constituent elements. In the printing apparatus 10, printing of images that include variable information, i.e., so-called variable data printing is performed, and images printed on the printing paper 9 (hereinafter referred to as "printed images") are automatically inspected. In the control part 14, data to be used in printing (hereinafter referred to as "original image data") is generated by rasterizing data of an image to be printed (hereinafter referred to as an "original image"). In this way, the control part 14 also functions as an image data generation part.

The conveying mechanism 12 conveys the printing paper 9 in the (−Y) direction in FIG. 1 relative to the printing mechanism 11. Note that the X, Y, and Z directions in FIG. 1 are perpendicular to one another, and the Z direction corresponds to the up-down direction. In the conveying mechanism 12, a plurality of rollers 121 that are each long in the X direction in FIG. 1 are arranged in the Y direction. A supply part 122 that holds a roll of the pre-print printing paper 9 and conveys the printing paper 9 from that roll toward the printing mechanism 11 is provided on the (+Y) side of the rollers 121. A roll-up part 123 that rolls up and holds a printed portion of the printing paper 9 in a roll is provided on the (−Y) side of the rollers 121. In the following description, paper that is simply referred to as the "printing paper 9" refers to the printing paper 9 that is being conveyed (i.e., the printing paper 9 on the rollers 121).

The printing mechanism 11 is disposed above the conveying mechanism 12 and fixed to a frame 151 that is provided on a base 15 so as to straddle the conveying mechanism 12. FIG. 2 is a bottom view of a single ejection part 111 in the printing mechanism 11. In FIG. 2, the direction of movement of the printing paper 9 relative to the ejection part 111 (i.e., (−Y) direction) is shown as the upward direction. In actuality, the printing mechanism 11 is provided with a plurality of ejection parts that respectively eject color inks of cyan (C), magenta (M), yellow (Y), and black (K) and are arranged in the Y direction. The ejection part 111 has a plurality of heads 112 arranged in a staggered configuration in a direction that is perpendicular to the movement direction of the printing paper 9 and is parallel to a printing surface of the printing paper 9 (i.e., X direction in FIGS. 1 and 2, which is a direction corresponding to the width of the printing paper 9 and thus hereinafter referred to as a "width direction"). In the bottom face of each head 112, a plurality of outlets 1121 are formed in an array at a fixed pitch in the width direction.

The heads 112 are each provided with piezoelectric elements in correspondence with the outlets 1121. By driving the piezoelectric elements, fine ink droplets are ejected from the outlets 1121 toward the printing paper 9. The distance between each pair of heads 112 that are adjacent in the width direction is accurately adjusted, and all the outlets 1121 included in the ejection part 111 are arranged at a fixed pitch across the entire printing area on the printing paper 9 in the width direction. In the printing apparatus 10, high-speed printing is performed in a single pass of the printing paper 9 under the ejection part 111 (so-called one-pass printing). Although in FIG. 2, the heads 112 are each provided with only five outlets 1121, in actuality a larger number of outlets 1121 are arranged. The heads 112 may be of a type that ejects fine droplets by applying heat to inks.

In the printing apparatus 10 in FIG. 1, in parallel with the movement of the printing paper 9 in the (−Y) direction by the conveying mechanism 12, the control part 14 controls ink ejection from the heads 112 of each color in accordance with the original image data to be printed. As a result, a color image to be printed that corresponds to one page is formed on a portion of the printing paper 9 that corresponds to one page of a printed material.

The image inspection apparatus 13 includes an image reading apparatus 131 that reads a printed image on the printed printing paper 9 (i.e., a printed portion of the printing paper 9), and an image inspection part 132 that inspects a printed image based on such a read image. The image reading apparatus 131 is located downstream of the printing mechanism 11.

FIG. 3 is a diagram of the image reading apparatus 131 as viewed from the width direction of the printing paper 9, showing a simplified internal configuration of the image reading apparatus 131. The image reading apparatus 131 includes a first line illumination part 21a, a second line illumination part 21b located on the (+Y) side of the first line illumination part 21a, and an imaging part 22 located above the first line illumination part 21a and the second line illumination part 21b. The first line illumination part 21a includes a plurality of light emitting diodes 211 arranged in the X direction, and a lens unit 212. Rays of light emitted from the light emitting diodes 211 are made uniform in the X direction and are linearly applied onto the printing paper 9 along an optical axis J1. Similarly, the second line illumination part 21b includes a plurality of light emitting diodes 211 and a lens unit 212, and rays of light emitted from the light emitting diodes 211 are made uniform in the X direction and are linearly applied to the same position as irradiated by the first line illumination part 21a along an optical axis J2. The imaging part 22 captures a linear area that is included in the area irradiated with the light by the first line illumination part 21a and the second line illumination part 21b. Hereinafter, the entire area captured by the imaging part 22 is referred to as an "imaging area 91". The imaging area 91 includes a range in which an image is printed, in the width direction.

Figure 4:
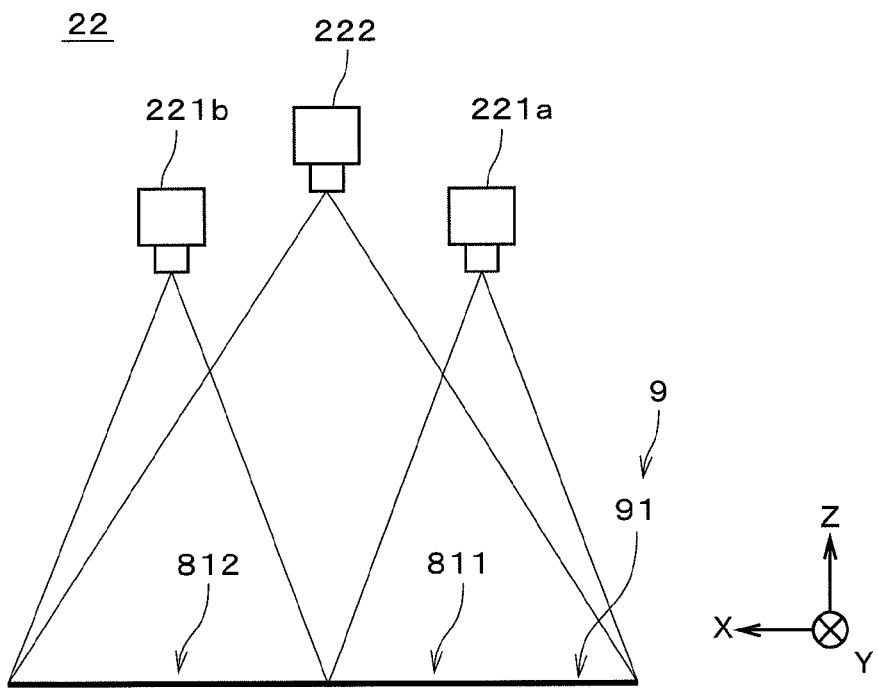
FIG. 4 shows the arrangement of cameras in the image reading apparatus.

FIG. 4 shows the arrangement of a plurality of cameras in the imaging part 22 when viewed from the Y direction in FIG. 3. It should be noted that an optical axis J3 in FIG. 3 is shown in a developed form in FIG. 4. The imaging part 22 includes two color line cameras 221a and 221b, a single monochrome line camera 222 (shown only in FIG. 4) positioned between the color line cameras 221a and 221b, a first mirror 223, and a second mirror 224 (both mirrors are shown only in FIG. 3). In the following description, when there is no need to distinguish between the color line cameras 221a and 221b, these cameras are referred to as "color line cameras 221", and when the color line cameras 221a and 221b need to be distinguished from each other, they are respectively referred to as a "first color line camera 221a" and a "second color line camera 221b".

The first mirror 223 has a strip-like shape that is long in the X direction, and is disposed under the color line cameras 221 and the monochrome line camera 222. The second mirror 224 also has a strip-like shape that is long in the X direction, and is located on the (−Y) side of the color line cameras 221 and the monochrome line camera 222. As shown in FIG. 3, in the imaging part 22, the optical axes of the color line cameras 221 and the optical axis of the monochrome line camera 222 are bent by the first mirror 223 and the second mirror 224. Furthermore, the optical axes of the color line cameras 221 and the optical axis of the monochrome line camera 222 are parallel to one another. In FIG. 3, the optical axes of the color line cameras 221 and the monochrome line camera 222 overlap one another and are given the reference numeral J3.

As shown in FIG. 4, the color line cameras 221 and the monochrome line camera 222 are arranged in the X direction, and the monochrome line camera 222 is located slightly above the color line cameras 221. A line sensor of each color line camera 221 has 4096 light receiving elements arranged in the X direction, each light receiving element having a dimension of 10 μm in the X direction. The lens unit of each color line camera has a focal length of 105 mm and a magnification ratio of 1/7.2.

A line sensor of the monochrome line camera 222 has 8192 light receiving elements arranged in the X direction, each light receiving element having a dimension of 7 μm in the X direction. The lens unit of the monochrome line camera has a focal length of 85 mm and a magnification ratio of 1/10.28. The color line cameras 221 and the monochrome line camera 222 have approximately the same working distance, and their field size per pixel in the X direction is 72 μm. In the imaging part 22, the resolving power of the color line cameras 221 in the width direction of the printing paper 9 is less than or equal to ½ times the resolution in the width direction of a printed image. As a result, it is possible to quickly and appropriately detect a defect in the printed image. Note that the resolving power and the resolution as used here refer to the number of pixels per unit distance. The resolving power of the monochrome line camera 222 is approximately the same as that of each color line camera 221.

In the color line cameras 221, the aperture values and exposure times are determined in synchronization with a change in the moving speed of the printing paper 9, and the resolving power is made constant even if the moving speed of the printing paper 9 changes. The same applies to the monochrome line camera 222. In order to acquire information elements described later, the monochrome line camera 222 has a resolving power of approximately 128 μm in the movement direction of the printing paper 9. Thus, when the moving speed of the printing paper 9 is 200 m per minute, the line rate of the monochrome line camera 222 (the imaging frequency per unit time) is greater than or equal to 25 kHz.

Light from the imaging area 91 enters the second mirror 224 along the optical axis J3, is reflected by the second mirror 224, and then guided to the first mirror 223. Light reflected by the first mirror 223 enters the color line cameras 221 and the monochrome line camera 222. In this way, the first mirror 223 and the second mirror 224 are common to an optical system between the color line cameras 221 and the imaging area 91 and an optical system between the imaging area 91 and the monochrome line camera 222.

As shown in FIG. 4, the right half of the imaging area 91 of the printing paper 9 is captured by the first color line camera 221a provided on the (−X) side. The left half of the imaging area 91 is captured by the second color line camera 221b provided on the (+X) side. In the imaging part 22, an imaging range 812 of the second color line camera 221b is aligned in a longitudinal direction of an imaging range 811 of the first color line camera 221a (i.e., the X direction in FIG. 4). As a result, the entire imaging area 91 is captured. In the case of the monochrome line camera 222, the entire imaging area 91 is an imaging range of the camera.

In the printing apparatus 10 shown in FIG. 1, the color line cameras 221 and the monochrome line camera 222 repeat their imaging operations while the printing paper 9 is continuously being moved in the moving direction by the conveying mechanism 12. Color images acquired by the color line cameras 221 and a monochrome image acquired by the monochrome line camera 222 are output to the image inspection part 132. In the following description, when there is no need to distinguish between color images and a monochrome image, the images are referred to as "captured images".

Figure 5:
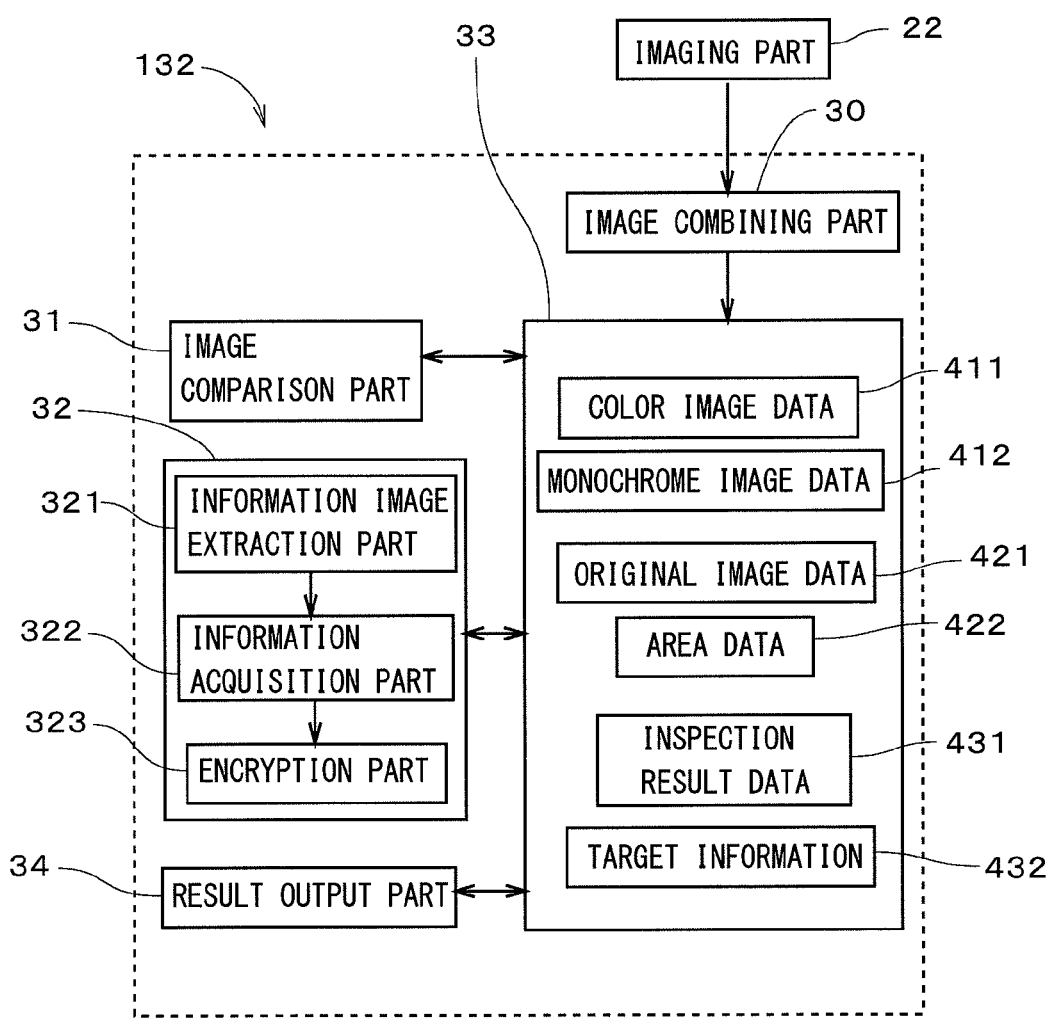
FIG. 5 shows a functional configuration of an image inspection part.

FIG. 5 is a block diagram showing a functional configuration of the image inspection part 132. Although in the present embodiment, the image inspection part 132 is implemented by a computer and a dedicated electric circuit, the image inspection part 132 as a whole may, of course, be implemented by either a computer or a dedicated electric circuit. The image inspection part 132 includes an image combining part 30 that combines images received from the imaging part 22, an image comparison part 31 that inspects the presence or absence of defects in printed images, an information reading part 32 that acquires information elements in printed images, a storage part 33 that stores various types of information, and a result output part 34 that outputs inspection results. The information elements as used here refer to characters such as alphabet letters, symbols, numbers such as Arabic numerals, or code patterns such as bar codes and two-dimensional codes, and represent character information such as the name of a customer or numerical information such as the amount of money received. A printed image printed on each page of the printing paper 9 includes at least one information element. In FIG. 5, storage devices such as a semiconductor memory and a hard disk driving device in the image inspection part 132 are collectively shown as the storage part 33.

The information reading part 32 includes an information image extraction part 321, an information acquisition part 322, and an encryption part 323. The functions of these parts will be described later.

Next, an operation for inspecting a printed image while printing an image on the printing paper 9, performed by the printing apparatus 10 will be described with reference to FIG. 6. First, the control part 14 shown in FIG. 1 generates original image data to be printed (step S11).

The original image data is transmitted to the printing mechanism 11, and the printing mechanism 11 controls ejection of each color ink in accordance with the original image data while the conveying mechanism 12 is continuously moving the printing paper 9. As a result, an image to be printed is formed on the printing paper 9 (step S12). Then, the printed image immediately after formed is captured by the image reading apparatus 131, and captured images are sequentially acquired (step S13). The captured images are output to the image inspection part 132.

In the image combining part 30 of the image inspection part 132, the outputs of the two color line cameras 221 are combined so as to generate a color image (step S14), and color image data 411 is stored in the storage part 33. The monochrome image captured with the monochrome line camera 222 is stored as monochrome image data 412 in the storage part 33. In parallel with the printing operation, the original image data 421 is transmitted from the control part 41 to the image inspection part 132 and stored in the storage part 33. At this time, the original image data 421 is converted from CMYK color space data to RGB color space data.

Next, in the image comparison part 31, the color image data 411 is compared with the original image data 421 (step S15). Through this, the presence or absence of defects, such as ink dripping or dot missing, in the printed image is inspected. The comparison result is stored as inspection result data 431 in the storage part 33 (step S16). The comparison result is further output to an operator via the result output part 34 such as a display part. Note that the inspection of the color image may be performed in units of several lines, instead of in units of pages. In the above description, in order to facilitate understanding, the color image data 411 and the original image data 421 are first stored in the storage part 33 and then compared by the image comparison part 31, but these pieces of image data may be directly input to and compared by the image comparison part 31 in units of line images.

In parallel with the inspection of the color image, the information image extraction part 321 of the information reading part 32 extracts a portion of the monochrome image that corresponds to an information element(s), as an information element image (step S21). In the image inspection part 132, area data 422 that indicates an area (a range) of the original image in which an information element(s) is present has been input in advance by an operator and is stored in the storage part 33. Note that, to be precise, the type of each information element (i.e., whether or not the information element is for optical character recognition (OCR), or the type of each code pattern) is also stored. In the control part 14 or the image inspection part 132, the area data 422 or the data indicating the type of information elements may be automatically generated from the original image data before rasterization.

In the information acquisition part 322, if an information element is a letter, a number, or a symbol, character information or numerical information indicated by the information element(s) is read by OCR from the information element image, and if the information element is a code pattern, the information element is decoded and read as character information or numerical information (step S22). The code pattern may be a pattern other than a bar code or a two-dimensional code.

Hereinafter, the character information or numerical information acquired from the information element image is referred to as "target information". In the present embodiment, since the target information is expressed in text form or a markup language and includes personal information, it is encrypted by the encryption part 323 (step S23). The encrypted target information 432 is stored in the storage part 33 (step S24).

If, on the other hand, the target information cannot be read in step S22, a number or the like that indicates the corresponding area is stored in the storage part 33, and an error indication is displayed on the result output part 34 so as to notify the operator of that fact (step S25).

In the printing operation performed by the printing apparatus 10, images to be printed that correspond to a large number of pages are continuously formed on the printing paper 9, and the image inspection apparatus 13 continuously performs defect inspection and target information acquisition on the printed image of each page immediately after the image has been formed.

Figure 7:
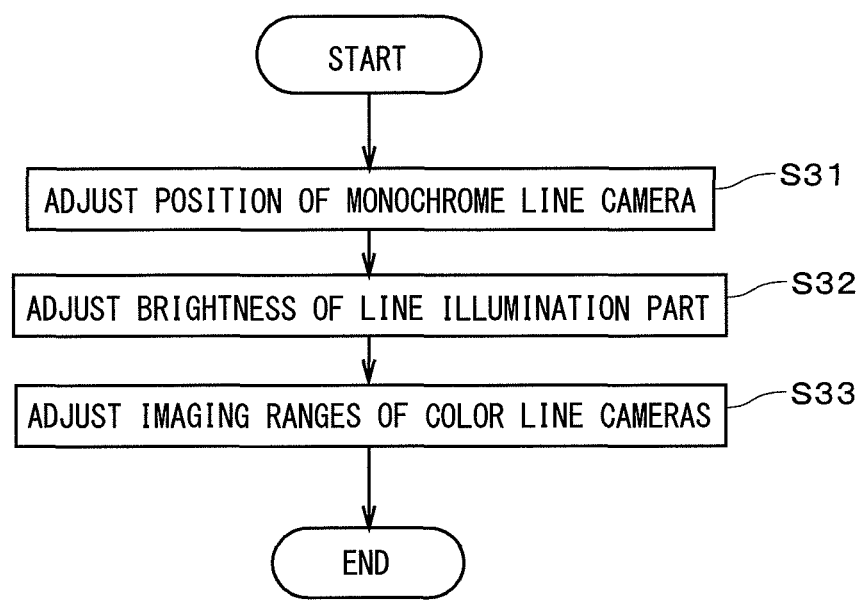
FIG. 7 is a flowchart of the procedure for adjusting the positions of the cameras.

Next, a method for adjusting the positions of the color line cameras 221 and the monochrome line camera 222 during assembly of the imaging part 22 will be described with reference to FIG. 7. First, the monochrome line camera 222 is positioned in approximately the center of the printing paper 9 in the width direction, and the first color line camera 221a and the second color line camera 221b are positioned on opposite sides of the monochrome line camera 222 in the width direction of the printing paper 9. Furthermore, a reference pattern for use as a reference is disposed at a position to be captured. The position of the monochrome line camera 222 is finely adjusted with reference to images captured with the monochrome line camera 222 (step S31). Next, the brightness of illumination by the first and second line illumination parts 21a and 21b shown in FIG. 3 is adjusted with reference to the output from the monochrome line camera 222 (step S32).

When the adjustment of the illumination has been completed, the reference pattern is captured with the first color line camera 221a, the second color line camera 221b, and the monochrome line camera 222. Then, the position of the imaging range of the first color line camera 221a in the X and Y directions is adjusted such that the image captured with the first color line camera 221a is the same as the right half in FIG. 4 of the pattern image captured with the monochrome line camera 222. Next, the position of the imaging range of the second color line camera 221a in the X and Y directions is adjusted such that the borders of the image captured with the second color line camera 221b and the image captured with the first color line camera 221a match (step S33).

With the above-described method, the two imaging ranges of the first and second color line cameras 221a and 221b are adjusted with reference to the outputs from the first and second color line cameras 221a and 221b and the monochrome line camera 222. This enables a joint portion between the two imaging ranges to be easily adjusted.

As described above, since in the printing apparatus 10, the imaging with the monochrome line camera 222 and the imaging with the color line cameras 221 are performed on the same imaging area 91, illumination during imaging can be implemented by a common line illumination part. As a result, the line illumination part becomes smaller, and it is possible to downsize the image reading apparatus 131. This also facilitates inline mounting of the image inspection apparatus 13 in the printing apparatus 10. Providing the first mirror 223 and the second mirror 224 enables the height of the imaging part 22 in the up-down direction to be reduced while retaining the working distance. Furthermore, commonly using the first mirror 223 and the second mirror 224 in the monochrome line camera 222 and the color line cameras 221 makes it possible to simplify the structure of the optical system and further downsize the image reading apparatus 131.

Normally, color line cameras have higher line rates (i.e., shorter scan cycles) than monochrome line cameras if they have the same number of pixels. However, in the image reading apparatus 131, because imaging is performed with the two color line cameras 221, the time taken to acquire a color image is shortened, and the overall reading speed of the imaging part 22 is improved. Accordingly, the image inspection apparatus 13 is, in particular, suitable for high-speed one-pass printing apparatuses. In addition, the manufacturing cost of the image reading apparatus 131 can be reduced by using the inexpensive color line cameras 221 having small numbers of pixels.

In the case where a portion of a printed image that corresponds to an information element(s) is divided and captured with a plurality of line cameras, a plurality of images need to be aligned and combined with high precision. In the image inspection part 132, since a monochrome image is acquired with the single monochrome line camera 222, image combining processing is unnecessary. This enables easy acquisition of the information element image.

Figure 8:
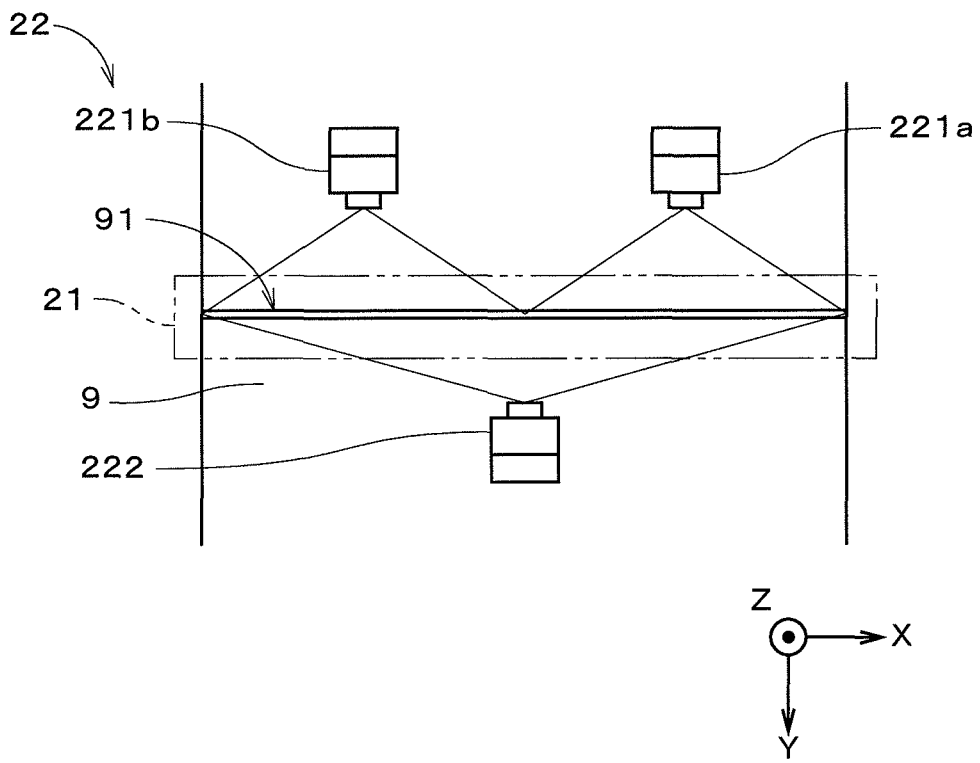
FIG. 8 shows an imaging part in another example.

FIG. 8 shows an imaging part 22 in another example, in which the direction from bottom to top in FIG. 8 is the direction of movement of the printing paper 9. In the imaging part 22, first and second color line cameras 221a and 221b and a monochrome line camera 222 are arranged back and front in the Y direction. The first color line camera 221a and the second color line camera 221b are arranged in the X direction. In FIG. 8, the optical axes of the color line cameras 221 and the monochrome line camera 222 are shown in a developed form. A single line illumination part 21 indicated by a double-dot-dash line is provided between the first and second color line cameras 221a and 221b and the monochrome line camera 222. The line illumination part 21 has a similar configuration to the first line illumination part 21a in FIG. 3, and light from the line illumination part 21 is linearly applied across the entire width of the printing paper 9.

Similarly to the case in FIG. 4, the imaging range of the monochrome line camera 222 matches the entire linear imaging area 91 to be captured. The imaging range of the first color line camera 221a corresponds to the right half of the imaging area 91 in FIG. 8, and the imaging range of the second color line camera 221b corresponds to the left half of the imaging area 91. In the imaging part 22 shown in FIG. 8 as well, illumination during imaging with the monochrome line camera 222 and imaging with the color line cameras 221 is implemented by the common line illumination part 21. Thus, it is possible to downsize the image reading apparatus 131.

Figure 9:
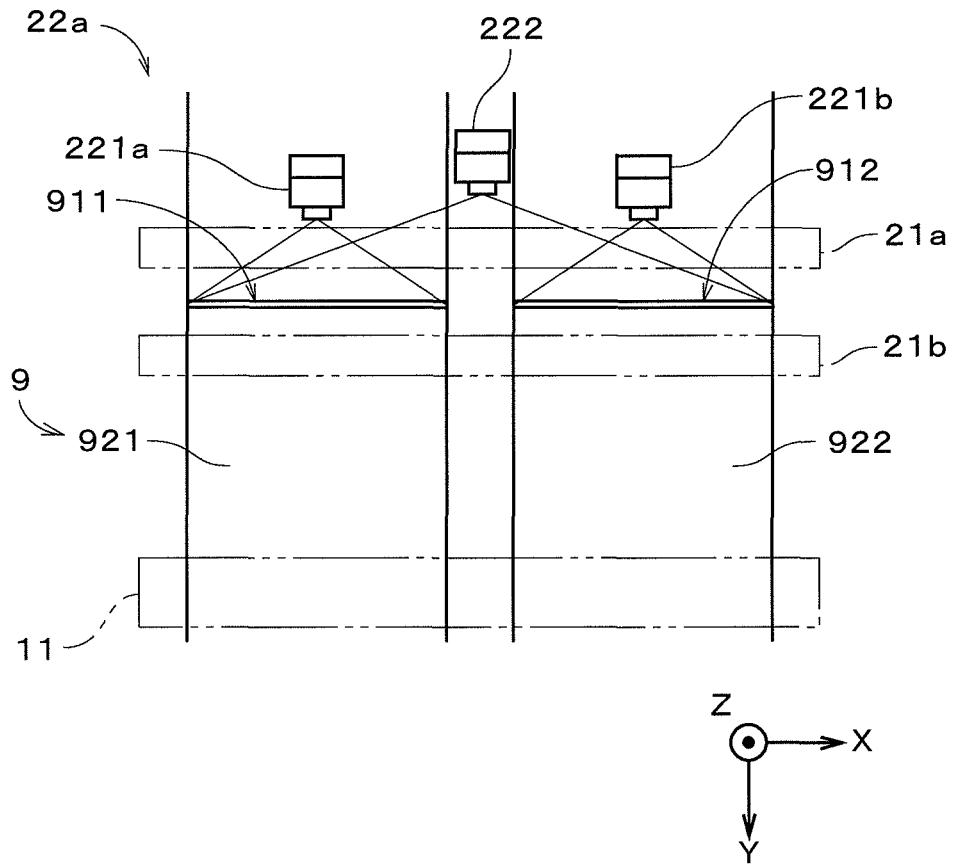
FIG. 9 shows an imaging part of a printing apparatus according to a second embodiment.

FIG. 9 shows an imaging part 22a of a printing apparatus according to a second embodiment. In FIG. 9, first and second line illumination parts 21a and 21b and a printing mechanism 11 are indicated by double-dot-dash lines. In the printing apparatus according to the second embodiment, double-side printing is performed on printing paper 9. The printing paper 9 is conveyed such that a portion of the paper with the front surface facing upward (hereinafter referred to as "first printing paper 921") is conveyed in the (−Y) direction on the left side in FIG. 9, and an image for the front surface is printed on the first printing paper 921 by the printing mechanism 11. The first printing paper 921 is then turned over, and the first printing paper 921 is returned to the (+Y) side in FIG. 9, i.e., upstream of the printing mechanism 11. Hereinafter, a portion of the printing paper that has been returned to the upstream side is referred to as "second printing paper 922". The second printing paper 922 is also conveyed in the (−Y) direction, and an image for the back surface is printed on the second printing paper 922 by the printing mechanism 11.

The imaging part 22a has a similar configuration to the imaging part 22 shown in FIGS. 3 and 4. The optical axes are shown in a simplified and developed form in FIG. 9. A first color line camera 221a, a monochrome line camera 222, and a second color line camera 221b are arranged in the X direction, and the first line illumination part 21a and the second line illumination part 21b are disposed on opposite sides of the imaging part 22a in the Y direction. The imaging part 22a uses the first and second color line cameras 221a and 221b that have smaller numbers of pixels than the monochrome line camera 222.

Linear light that extends in the width direction across the first printing paper 921 and the second printing paper 922 is applied by the first and second line illumination parts 21a and 21b. The imaging range of the first color line camera 221a is the entire imaging area 911 extending in the width direction on the first printing paper 921, and the imaging range of the second color line camera 221b is the entire imaging area 912 extending in the width direction on the second printing paper 922. The imaging range of the monochrome line camera 222 includes the imaging areas 911 and 912 of the first printing paper 921 and the second printing paper 922.

Figure 6:
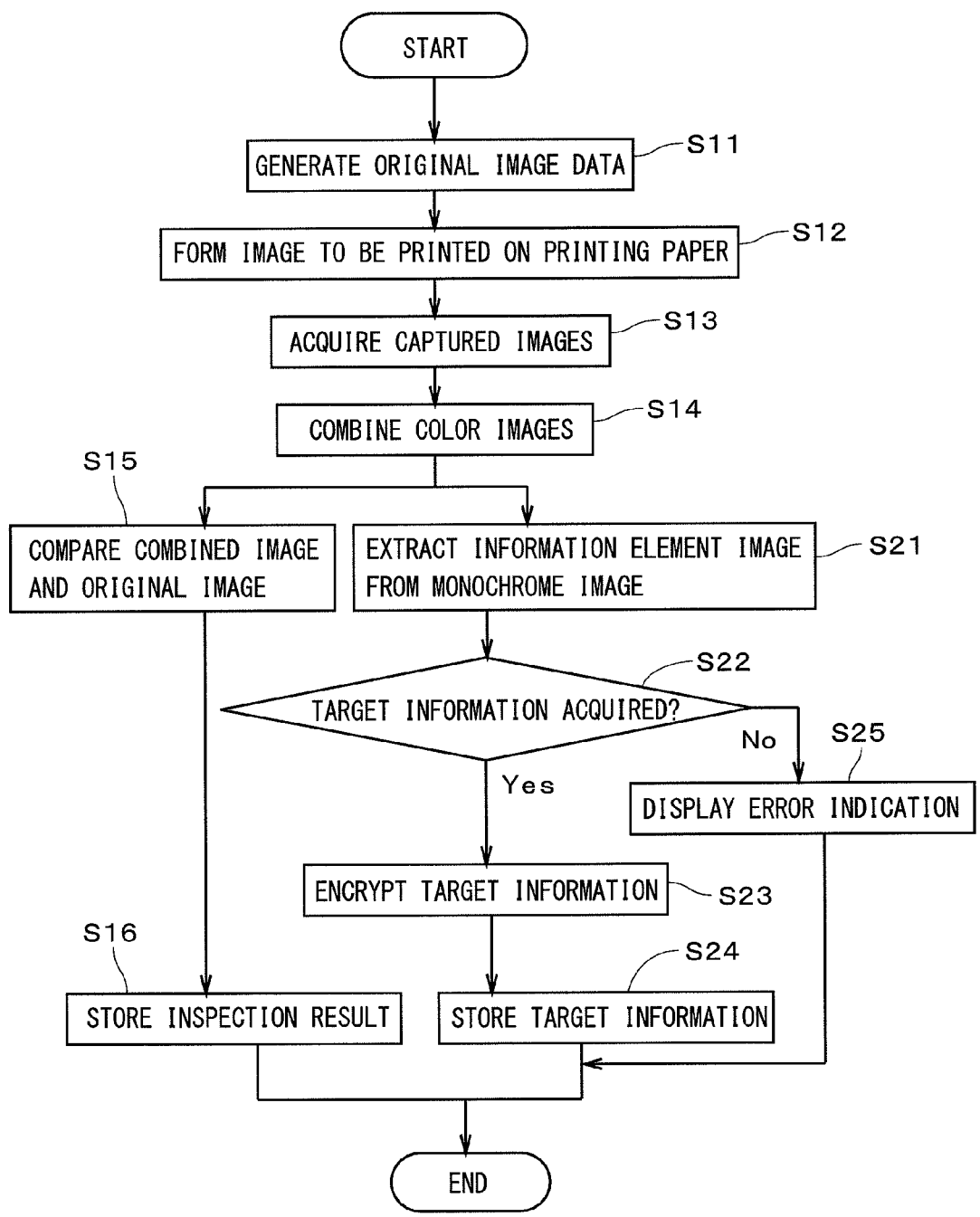
FIG. 6 is a flowchart of operations performed by the printing apparatus.

In the image inspection part 132, the image combining part 30 is not used, and a defect in the front-surface printed image is inspected based on the color image acquired with the first color line camera 221a, and a defect in the back-surface printed image is inspected based on the color image acquired with the second color line camera 221b (see steps S13, S15, and S16 in FIG. 6). Furthermore, target information is acquired from the printed image on the front surface based on a portion of the monochrome image that corresponds to the imaging area 911 on the first printing paper 921, the monochrome image having been acquired with the monochrome line camera 222, and another target information is acquired from the printed image on the back surface based on a portion of the monochrome image that corresponds to the imaging area 912 on the second printing paper 921 (see steps S21 to S25).

In the second embodiment as well, the color line cameras 221 and the monochrome line camera 222 use the common line illumination part in order to perform imaging. As a result, it is possible to downsize the image reading apparatus 131. By providing the two color line cameras 221, it is possible to secure the reading speeds of the color line cameras 221 and to thereby improve the overall reading speed of the imaging part 22. Using the inexpensive color line cameras 221 with small numbers of pixels enables a reduction in the manufacturing cost of the image reading apparatus 131.

Figure 10:
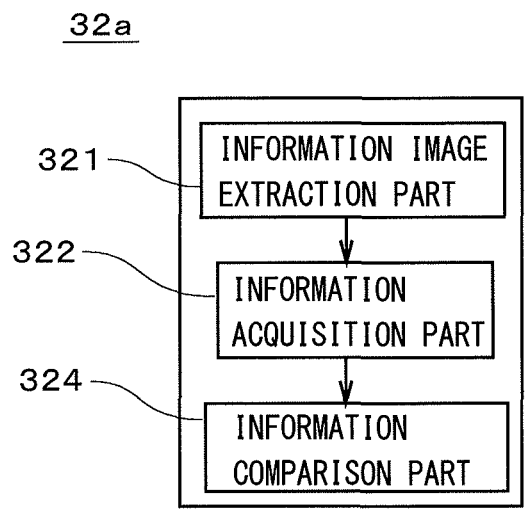
FIG. 10 shows an information inspection part of a printing apparatus according to a third embodiment.
Figure 11:
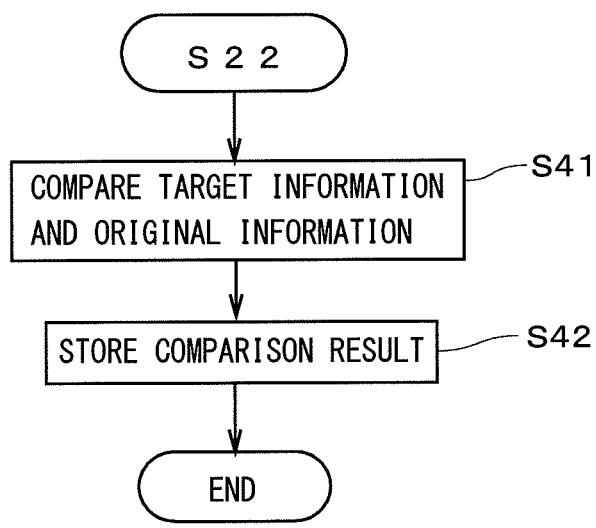
FIG. 11 is a flowchart of the procedure for inspecting an information element.

FIG. 10 shows part of an image inspection apparatus 13 in a printing apparatus according to a third embodiment. An information inspection part 32a shown in FIG. 10 is provided in the image inspection part 132, instead of the information reading part 32 shown in FIG. 5. In the information inspection part 32a, the encryption part 323 shown in FIG. 5 has been omitted, and an information comparison part 324 is provided. Furthermore, steps S41 and S42 shown in FIG. 11 are executed, instead of steps S23 and S24 in FIG. 6. The other part of the configuration of the printing apparatus according to the third embodiment is similar to that of the printing apparatus 10 according to the first embodiment, and the operation performed by the printing apparatus 10 is also similar to that in the first embodiment, with the exception that the target information is also inspected.

In the third embodiment, first, the control part 14 shown in FIG. 1 generates data that indicates an information element image based on original information, and the generated data is included in original image data (step S11). Then, in parallel with printing (step S12), the original image data and the original information are stored in the storage part 33 in FIG. 5. Here, the original information refers to character information such as the name of a customer, or numerical information such as the amount of money received.

When the image reading apparatus 131 has captured a printed image, the image inspection part 132 performs inspection of a color image, and the inspection result is stored in the storage part 33 (steps S13 to S16). From a monochrome image, an information element image is extracted by the information image extraction part 321 (step S21). The information acquisition part 322 acquires target information indicated by an information element(s) from the information element image (step S22). When the acquisition of target information is not possible, an error indication is displayed (step S25).

When the target information has been acquired, the information comparison part 324 compares the target information with the original information used in printing (step S41). The comparison result is included in the inspection result data 431 shown in FIG. 5 and stored in the storage part 33 (step S42). If the target information and the original information match completely, the result output part 34 outputs to an operator a result that indicates normality, and if they do not match completely, the result output part 34 outputs a result that indicates abnormality (failure).

In the third embodiment, providing the information comparison part 324 enables real-time inspection of an information element(s). Furthermore, as in the first embodiment, it is possible to reduce the size and manufacturing cost of the image reading apparatus 131 while improving the reading speed.

Figure 12:
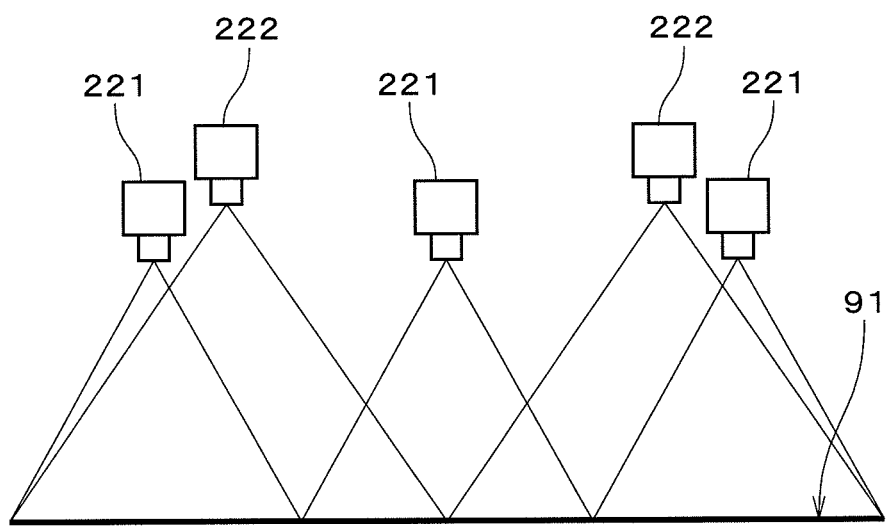
FIG. 12 shows another example of the arrangement of cameras in the imaging part.

While the above has been a description of embodiments of the present invention, the present invention is not limited to the above-described embodiments and can be modified in various ways. For example, as shown in FIG. 12, three color line cameras 221 and two monochrome line cameras 222 may be used to perform imaging. The imaging ranges of the two monochrome line cameras 222 are aligned in their longitudinal direction and overlap with the entire imaging area 91 on the printing paper 9. The imaging ranges of the three color line cameras 221 are also aligned in their longitudinal direction and overlap with the entire imaging area 91 on the printing paper 9. In this way, the imaging part may be provided with a plurality of monochrome line cameras 222 and a plurality of color line cameras 221, and the number of color line cameras 221 is greater than the number of monochrome line cameras 222. Furthermore, inexpensive color line camera having smaller numbers of pixels than each monochrome line camera 222 is used as each color line camera 221.

In the imaging part, the total number of pixels in the color line cameras 221 is preferably the same as the total number of pixels in all monochrome line cameras 222. However, the total numbers of pixels do not necessarily have to be the same in a strict sense.

In the above-described embodiments, parts of the imaging ranges of a plurality of color line cameras 221 may overlap with one another. The same applies to the case of providing a plurality of monochrome line cameras.

In the above-described first embodiment, at the time of defect inspection, the image captured with the first color line camera 221a and the image captured with the second color line camera 221b may be directly compared with corresponding portions of the original image data, without being combined with each other. In this case, for example, the original image data from the control part 14 is branched or divided in accordance with the number of color line cameras and stored in the storage part 33.

The image inspection part 132 may be implemented by the control part 14. In the above-described embodiments, the information element image and the portion other than the information element image may be printed separately (i.e., exclusively), or may be printed overlapping each other.

In the above-described embodiments, in addition to the first and second mirrors 223 and 224, other optical elements such as lenses may be common to the optical system between the first and second color line cameras 221a and 221b and the printing paper 9 and the optical system between the monochrome line camera 222 and the printing paper 9. Commonly using at least one optical element enables the structures of the optical systems to be simplified.

In the printing apparatus 10, the imaging area 91 does not necessarily have to be set along the width direction of the printing paper 9 in a strict sense, and may be inclined with respect to the width direction as long as the imaging area 91 is along a direction that is crossing with the direction of relative movement of the printing paper 9. Furthermore, the outlets 1121 of the heads 112 also do not necessarily have to be strictly arranged in the width direction of the printing paper 9, and they may be inclined with respect to the width direction as long as they are along a direction crossing with the direction of relative movement of the printing paper 9. The image inspection apparatus 13 may be used in other printing apparatuses that perform non-plate printing such as electrophotographic printing, besides inkjet printing apparatuses. The printing medium used in the printing apparatus 10 may be a film- or plate-like member, instead of printing paper. Furthermore, a configuration is also possible in which the position of the printing medium is fixed and the printing mechanism 11 and the image reading apparatus 131 are moved.

While the invention has been shown and described in detail, the foregoing description is in all aspects illustrative and not restrictive. It is therefore understood that numerous modifications and variations can be devised without departing from the scope of the invention.

REFERENCE SIGNS LIST

9 Printing paper
10 Printing apparatus
11 Printing mechanism
12 Conveying mechanism
13 Image inspection apparatus 14 Control part
21, 21a, 21b Line illumination part
31 Image comparison part
33 Storage part
34 Result output part
91, 911, 912 Imaging area
112 Head
122 Supply part
123 Roll-up part
131 Image reading apparatus
221, 221a, 221b Color line camera
222 Monochrome line camera
321 Information image extraction part
322 Information acquisition part
323 Encryption part
324 Information comparison part
1121 Outlet
J1 to J3 Optical axis

The invention claimed is:

1. A printing apparatus comprising:
a conveying mechanism that conveys a printing medium;
a printing mechanism that performs printing on said printing medium; and
an image inspection apparatus including an image reading apparatus, wherein
said printing mechanism includes a head in which ink outlets are arranged in a direction crossing with a conveying direction of said printing medium,
printing is performed in a single pass of said printing medium through said head while said head is ejecting fine droplets of ink,
said image reading apparatus comprises:
a line illumination part that applies light onto a linear imaging area on a printing medium, said imaging area extending in a direction crossing with a direction of relative movement of said printing medium;
one monochrome line camera that captures said imaging area, or a plurality of monochrome line cameras that capture said imaging area with imaging ranges of the cameras being aligned in a longitudinal direction of said imaging ranges; and
a plurality of color line cameras that capture said imaging area with imaging ranges of the cameras being aligned in a longitudinal direction thereof,
the number of said plurality of color line cameras is greater than the number of said one or plurality of monochrome line cameras, and
each color line camera has a smaller number of pixels than each monochrome line camera, resolving power of each monochrome line camera is approximately the same as that of each color line camera, and
said image inspection apparatus comprises:
an information image extraction part that extracts an information element image from an image acquired with said one or plurality of monochrome line cameras, said information element image being a portion corresponding to an information element(s) that is at least one of letters, numbers, symbols, and bar code patterns;
an information acquisition part that acquires target information from said information element image, said target information being character information or numerical information indicated by said information element(s);
a storage part that stores said target information; and
an image comparison part that compares an image acquired with said plurality of color line cameras and an image indicated by data used in printing.

2. The printing apparatus according to claim 1, further comprising:
an information comparison part that compares said target information and original information used in printing of said information element image.

3. The printing apparatus according to claim 2, further comprising:
an image data generation part that generates an information element image from original information, said information element image indicating at least one of letters, numbers, symbols, and bar code patterns, and generates and transmits data of an image to be printed that includes said information element image, to said printing mechanism.

4. The printing apparatus according to claim 1, further comprising:
an encryption part that encrypts said target information,
wherein said target information is expressed in text form or a markup language, and
said target information that has been encrypted is stored in said storage part.

5. The printing apparatus according to claim 1, wherein
an optical axis of said one or plurality of monochrome line cameras and optical axes of said plurality of color line cameras are parallel to each other, and
at least one optical element is common to an optical system between said one or plurality of monochrome line cameras and said printing medium and an optical system between said plurality of color line cameras and said printing medium.

6. The printing apparatus according to claim 1, wherein
said one or plurality of monochrome line cameras is one monochrome line camera.

7. The printing apparatus according to claim 2, wherein
said one or plurality of monochrome line cameras is one monochrome line camera.

8. The printing apparatus according to claim 3, wherein
said one or plurality of monochrome line cameras is one monochrome line camera.

9. The printing apparatus according to claim 4, wherein
said one or plurality of monochrome line cameras is one monochrome line camera.

10. The printing apparatus according to claim 5, wherein
said one or plurality of monochrome line cameras is one monochrome line camera.

11. The printing apparatus according to claim 1, wherein
said conveying mechanism includes:
a supply part that holds a roll of said printing medium that has not undergone printing and conveys said printing medium from said roll toward said printing mechanism; and
a roll-up part that rolls up a printed portion of said printing medium.

12. The printing apparatus according to claim 2, wherein
said conveying mechanism includes:
a supply part that holds a roll of said printing medium that has not undergone printing and conveys said printing medium from said roll toward said printing mechanism; and
a roll-up part that rolls up a printed portion of said printing medium.

13. The printing apparatus according to claim 3, wherein
said conveying mechanism includes:
a supply part that holds a roll of said printing medium that has not undergone printing and conveys said printing medium from said roll toward said printing mechanism; and a roll-up part that rolls up a printed portion of said printing medium.

14. The printing apparatus according to claim 4, wherein said conveying mechanism includes:

a supply part that holds a roll of said printing medium that has not undergone printing and conveys said printing medium from said roll toward said printing mechanism; and a roll-up part that rolls up a printed portion of said printing medium.

15. The printing apparatus according to claim 5, wherein said conveying mechanism includes:

a supply part that holds a roll of said printing medium that has not undergone printing and conveys said printing medium from said roll toward said printing mechanism; and a roll-up part that rolls up a printed portion of said printing medium.

16. The printing apparatus according to claim 6, wherein said conveying mechanism includes:

a supply part that holds a roll of said printing medium that has not undergone printing and conveys said printing medium from said roll toward said printing mechanism; and a roll-up part that rolls up a printed portion of said printing medium.

\* \* \* \* \*